(12) United States Patent
Li et al.

(10) Patent No.: US 11,266,415 B2
(45) Date of Patent: Mar. 8, 2022

(54) LUNG VOLUME REDUCTION ELASTIC IMPLANT AND LUNG VOLUME REDUCTION INSTRUMENT

(71) Applicant: Lifetech Scientific (Shenzhen) Co., Ltd., Shenzhen (CN)

(72) Inventors: Anning Li, Shenzhen (CN); Siyi Li, Shenzhen (CN)

(73) Assignee: Shenzhen Lifetech Respiration Scientific Co. Ltd., Shenzhen (CN)

(*) Notice: Subject to any disclaimer, the term of this patent is extended or adjusted under 35 U.S.C. 154(b) by 217 days.

(21) Appl. No.: 16/474,728

(22) PCT Filed: Dec. 19, 2017

(86) PCT No.: PCT/CN2017/117181
§ 371 (c)(1),
(2) Date: Jun. 28, 2019

(87) PCT Pub. No.: WO2018/121346
PCT Pub. Date: Jul. 5, 2018

(65) Prior Publication Data
US 2020/0383687 A1  Dec. 10, 2020

(30) Foreign Application Priority Data

Dec. 30, 2016  (CN) .......................... 201611263514.1

(51) Int. Cl.
*A61B 17/12* (2006.01)
*A61B 90/00* (2016.01)
*A61B 17/00* (2006.01)

(52) U.S. Cl.
CPC .. *A61B 17/12104* (2013.01); *A61B 17/00234* (2013.01); *A61B 17/1214* (2013.01);
(Continued)

(58) Field of Classification Search
CPC .................. A61B 90/08; A61B 90/39; A61B 2090/08021; A61B 2090/3966;
(Continued)

(56) References Cited

U.S. PATENT DOCUMENTS 6,652,556 B1 * 11/2003 VanTassel ........ A61B 17/12172
606/200
7,654,998 B1 * 2/2010 Ingenito ................. A61K 45/06
604/514

(Continued)

FOREIGN PATENT DOCUMENTS

CN 106580527 A 10/2015
CN 106691626 A 11/2015
(Continued)

OTHER PUBLICATIONS

International Search Report dated Mar. 27, 2018 for corresponding PCT Application No. PCT/CN2017/117181.
(Continued)

*Primary Examiner* — Melanie R Tyson
*Assistant Examiner* — Paige A Codrington
(74) *Attorney, Agent, or Firm* — Raymond Sun

(57) ABSTRACT

A lung volume reduction elastic implant (500) and a lung volume reduction instrument are provided. The lung volume reduction elastic implant (500) has an elastic deformation part (51), and a flexible guide (53, 53*a*) connected to the distal end of the elastic deformation part (51). The flexible guide (53, 53*a*) is provided with a first flexible part (531). The first flexible part (531) has an insert part (5312) and a distal part (5311). The insert part (5312) is connected to the distal end of the elastic deformation part (51). The distal end of the distal part (5311) of the first flexible part (531) is the distal end of the lung volume reduction elastic implant (500). The first flexible part (531) is internally provided with
(Continued)

a radiograph component (56). The lung volume reduction elastic implant (500) and the lung volume reduction instrument use the implant (500) to provide a sufficient bending force while maintaining better flexibility, reducing the risk of bronchus contusion when the implant (500) is bent after the implant (500) is implanted into a bronchial tube, and enhancing the safety of lung volume reduction surgery.

19 Claims, 12 Drawing Sheets

(52) U.S. Cl.
CPC .............. *A61B 90/08* (2016.02); *A61B 90/39* (2016.02); *A61B 2017/00309* (2013.01); *A61B 2017/00809* (2013.01); *A61B 2017/00995* (2013.01); *A61B 2017/1205* (2013.01); *A61B 2090/08021* (2016.02); *A61B 2090/3966* (2016.02)

(58) Field of Classification Search
CPC ........ A61B 17/12104; A61B 17/00234; A61B 17/1214; A61B 2017/00309; A61B 2017/00809; A61B 2017/00995; A61B 2017/1205; A61B 17/12154; A61B 17/12022; A61B 17/12027; A61B 17/1205; A61B 17/12036; A61B 17/1204; A61B 17/12031; A61B 2017/00663; A61B 2017/00862; A61B 2017/0618; A61B 2017/06171; A61B 2017/06185; A61F 2/82; A61F 2/91; A61F 2/04
USPC ........................................................ 606/191
See application file for complete search history.

(56) References Cited

U.S. PATENT DOCUMENTS

| | | | | |
|---|---|---|---|---|
| RE42,756 E | * | 9/2011 | Guglielmi | A61M 25/09 606/32 |
| 8,632,605 B2 | * | 1/2014 | Thompson | A61B 17/24 623/23.65 |
| 9,173,669 B2 | | 11/2015 | Mathis et al. | |
| 10,206,821 B2 | * | 2/2019 | Campbell | A61B 17/00234 |
| 10,342,549 B2 | | 7/2019 | Lin et al. | |
| 10,687,821 B2 | | 6/2020 | Li et al. | |
| 10,905,538 B2 | | 2/2021 | Li et al. | |
| 2001/0051799 A1 | * | 12/2001 | Ingenito | A61K 38/1858 604/516 |
| 2003/0228344 A1 | * | 12/2003 | Fields | A61F 2/04 424/423 |
| 2004/0109823 A1 | * | 6/2004 | Kaplan | A61L 31/146 424/1.11 |
| 2008/0097401 A1 | * | 4/2008 | Trapp | A61B 17/1214 604/527 |
| 2009/0062927 A1 | * | 3/2009 | Marten | A61F 2/203 623/23.65 |
| 2009/0076622 A1 | | 3/2009 | Thompson | |
| 2010/0130850 A1 | * | 5/2010 | Pakter | A61B 10/0241 600/411 |
| 2011/0152678 A1 | * | 6/2011 | Aljuri | A61B 5/055 600/427 |
| 2015/0265283 A1 | * | 9/2015 | Lean | A61B 18/1492 623/23.65 |
| 2015/0265799 A1 | * | 9/2015 | Smith | A61B 17/12186 604/514 |
| 2017/0136222 A1 | * | 5/2017 | Hakim | A61F 2/82 |
| 2017/0367810 A1 | * | 12/2017 | Tanaka | A61F 2/04 |
| 2018/0132860 A1 | * | 5/2018 | Lin | A61B 17/12145 |
| 2018/0296221 A1 | * | 10/2018 | Jiang | A61B 17/12022 |
| 2019/0000667 A1 | * | 1/2019 | Dollberg | A61B 18/06 |
| 2021/0093324 A1 | | 4/2021 | Li et al. | |

FOREIGN PATENT DOCUMENTS

| | | | | |
|---|---|---|---|---|
| CN | 105455930 A | | 4/2016 | |
| CN | 108210133 A | | 12/2016 | |
| WO | WO03041779 A1 | | 5/2003 | |
| WO | WO-2015188705 A1 | * | 12/2015 | ............... A61F 2/86 |

OTHER PUBLICATIONS

Office Action for corresponding China Application No. 201611263514.1.
Search Report for corresponding China Application No. 201611263514.1.
European Search Report dated Aug. 13, 2020 for corresponding European Application No. 17 88 7300.
Office Action dated Mar. 16, 2021 for corresponding India Application No. 201917027905.
First Office Action for corresponding China Application No. 201611263514.1.
Second Office Action for corresponding China Application No. 201611263514.1.

* cited by examiner

LUNG VOLUME REDUCTION ELASTIC IMPLANT AND LUNG VOLUME REDUCTION INSTRUMENT

TECHNICAL FIELD

The present disclosure belongs to the technical field of interventional therapy, relates to an implant and an instrument for the interventional therapy, and more particularly relates to a lung volume reduction elastic implant and a lung volume reduction instrument.

BACKGROUND ART

Pulmonary emphysema is a common pulmonary disease. Traditional internal therapies for pulmonary emphysema include oxygen inhalation, pulmonary infection prevention, bronchus spasm relaxation and the like, but produce extremely limited therapeutic effect. Surgical therapies for pulmonary emphysema mostly adopt lung volume reduction surgery, and also have limitations, for example: strict surgical indications, risks of many complications, anesthesia and anesthesia-related complications, difficulty in predicting therapeutic effect before the surgery, and a possibly irreparable undesired therapeutic effect caused by over-cutting or sub-cutting after the surgery, high surgical costs, and mental and physical sufferings. In addition, some patients will not be able to tolerate the surgery due to their poor lung functions, thereby leading to a higher postoperative mortality rate, which limits the use of surgical therapies.

To better treat pulmonary emphysema, improve the quality of life for a patient, and reduce trauma to the patient during surgery, interventional modes for treating pulmonary emphysema, such as the modes of applying a one-way valve, biogel, steam thermal ablation, or an elastic coil with the help of a bronchoscope, have been researched and utilized internationally. However, the one-way valve interventional mode produces poor clinical effect because of the failure in effectively and actively expelling residual gas and sputum in a target region, and its therapeutic effect is restricted by technical difficulties in collateral ventilation and the requirement for precise placement of the one-way valve at different anatomical structure positions. The problem of postoperative inflammation caused by biogel interventional mode due to a fully blocked emphysema region has not been properly solved. Steam thermal ablation would result in postoperative inflammation due to the destruction of original tissue structure of the emphysema region.

At the present time, an updated therapeutic method for pulmonary emphysema is a method of implanting an elastic coil, serving as an implant, into a lesion locus of a human lung. FIG. 1 is a schematic diagram of a lung volume reduction elastic coil in the prior art. This product is made of a nickel-titanium memory alloy metal wire, and may elastically deform under the action of an external force. Under the restriction of a delivery system, this product may be implanted in a straight line form into the lung through a working channel of the bronchoscope. After being delivered into a bronchus of a pulmonary emphysema region, the coil is released from the restriction of the delivery system and then recovers its natural shape (a shape in the absence of the external force) as shown in FIG. 1, and at the same time, the emphysema region is squeezed under the pulling action of the nickel-titanium alloy wire to exhaust gas in the bronchus and reduce the volume of the lung tissue in the pulmonary emphysema region. Therefore, a relatively healthy lung tissue therearound may better exert a physiological function.

The above-mentioned implant has the following defects: to achieve a relatively good squeezing volume reduction effect, the implant is generally made of a metal elastic coil with relatively high elasticity, and has a high degree of hardness and has a low degree of flexibility, so it easily causes injury to the bronchus when implanted into the bronchus.

SUMMARY OF THE INVENTION

In view of the above-mentioned defects in the prior art, the present disclosure provides an implant that has a relatively high degree of flexibility so as to solve the above technical problems. After the implant of the present disclosure is implanted into a bronchus, the risk of bruising the bronchus during bending of the implant may be reduced, and the safety of lung volume reduction surgery is improved.

To further solve the technical problem, in view of the above-mentioned defects in the prior art, the present disclosure provides a lung volume reduction instrument which can implant the implant into a lung bypass, or the ends of some small-diameter tracheas, according to specific clinical requirements so as to ensure safer surgical operation and to achieve a better therapeutic effect.

A technical scheme adopted by the present disclosure is as follows:

a lung volume reduction elastic implant, including an elastic deformation part and a flexible guide part connected with a distal end of the elastic deformation part. The flexible guide part is provided with a first flexible section. The first flexible section includes an insert section and a distal section. The insert section is connected with the distal end of the elastic deformation part. A distal end of the distal section of the first flexible section is a distal end of the lung volume reduction elastic implant. A radiograph component is arranged in the first flexible section.

In one embodiment of the technical solution, the flexible guide part further includes a hollow second flexible section connected between the elastic deformation part and the first flexible section. The insert section of the first flexible section is inserted into the second flexible section, and a proximal end of the radiograph component is inserted into the second flexible section along with the insert section of the first flexible section. In one embodiment of the technical solution, the radial height of the insert section of the first flexible section is less than that of the distal section, and a joint of the insert section and the distal section has a stepped shape.

In one embodiment of the technical solution, the proximal end of the radiograph component is closer to a distal end of the distal section than a proximal end of the insert section, and a perpendicular distance between the proximal end of the radiograph component and a proximal end of the first flexible section is 0.5 mm to 20 mm.

In one embodiment of the technical solution, the radiograph component includes a radiograph wire arranged in the first flexible section.

In one embodiment of the technical solution, the radiograph component further includes a radiograph ring connected to a distal end of the radiograph wire.

In one embodiment of the technical solution, under the action of the same external force, the second flexible section deforms more easily from a proximal end to a distal end.

In one embodiment of the technical solution, the second flexible section includes a tubular body cut from a nickel-titanium tube and having continuous spiral cutting slots.

In one embodiment of the technical solution, the distance between two adjacent cutting slots of the second flexible section along the axial direction of the second flexible section is gradually increased from the distal end to the proximal end of the second flexible section.

In one embodiment of the technical solution, the lung volume reduction elastic implant has an opening in a proximal end and further includes a boss connected with a proximal end of the elastic deformation part. The superelastic elastic deformation part is provided with a plurality of cutting slots in a spaced-apart manner along the longitudinal direction of the elastic deformation part. Each cutting slot communicates with a lumen of the elastic deformation part. Under the action of the same external force, the flexible guide part deforms more easily than the elastic deformation part. An outer diameter of the boss is greater than that of a part of the elastic implant that is close to the boss in a delivery state.

In one embodiment of the technical solution, the elastic implant further includes a connection part located between the elastic deformation part and the boss. Under the action of the same external force, the connection part deforms more easily than the elastic deformation part.

In one embodiment of the technical solution, the connection part is provided with a plurality of cutting slots in a spaced-apart manner along the longitudinal direction of the connection part.

In one embodiment of the technical solution, the connection part includes multiple hollow sub components connected end to end. A proximal end of each hollow sub component includes multiple proximal end protrusions distributed along the circumferential direction of the hollow sub component. The circumferential length of each proximal end protrusion from a proximal end to a distal end is gradually decreased, and a proximal end groove is formed between two adjacent proximal end protrusions. A distal end of each hollow sub component includes multiple distal end protrusions distributed along the circumferential direction of the hollow sub component. The circumferential length of each distal end protrusion from a proximal end to a distal end is gradually increased, and a distal end groove is formed between two adjacent distal end protrusions.

In one embodiment of the technical solution, from the distal end to the proximal end of the flexible guide part, part of a distal-end face of the boss is sunken towards a proximal end of the boss to form an annular groove surrounding the longitudinal center line of the boss.

In one embodiment of the technical solution, part of a side surface of the boss is sunken into the inner of the boss to form an annular groove surrounding the longitudinal center line of the boss.

In one embodiment of the technical solution, the boss includes multiple small protrusions distributed in a spaced-apart manner along the circumferential direction of the boss.

The present disclosure further provides a lung volume reduction instrument, including any one of the above-mentioned implants, and a delivery apparatus matched with the implant. The delivery apparatus includes a core wire and a delivery mechanism. A proximal end of the implant is detachably connected to a distal end of the delivery mechanism. The core wire may be movably arranged in and extends through a lumen of the implant and a lumen of the delivery mechanism.

In one embodiment of the technical solution, a core wire guide head coaxial with the core wire is arranged at a distal end of the core wire, and an outer diameter of the core wire guide head is consistent with that of the core wire.

In one embodiment of the technical solution, the core wire guide head includes a guide column and a spring arranged on and surrounding the guide column. The guide column and the core wire are made from one piece, or the guide column is fixedly connected to the distal end of the core wire. The spring is provided with a radiopaque marker.

In one embodiment of the technical solution, the proximal end of the implant is detachably connected with the distal end of the delivery mechanism.

The implant of the present disclosure includes the elastic deformation part and the flexible guide part connected with the distal end of the elastic deformation part. The flexible guide part is provided with a first flexible section having relatively high flexibility. The distal end of the distal section of the first flexible section serves as the distal end of the lung volume reduction elastic implant in the present disclosure; compared with the prior art, after the implant is implanted into a bronchus, as the first flexible section is more flexible than a metal and has high elasticity, when the first flexible section is stressed, it will bend more easily because of its higher flexibility and has a relatively soft surface, so injury caused by the lung volume reduction elastic implant to a lung tissue can be greatly reduced.

BRIEF DESCRIPTION OF THE DRAWINGS

The present disclosure will be further described below in combination with the accompanying drawings and embodiments. In the drawings.

Figure 1:
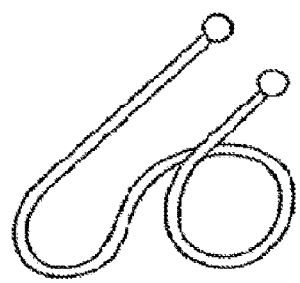
FIG. 1 is a structural schematic diagram of an elastic coil in the prior art.

Numerals in the drawings: 51: elastic deformation part; 53: flexible guide part; 52: connection part; 57: connection member; 55: elastic thin film; 531: first flexible section; 532: second flexible section; 500: elastic implant; 56: radiograph component; 511: proximal end of the elastic deformation part; 513: distal end of the elastic deformation part; 56: radiograph component; 561: radiograph wire; and 562: radiograph ring.

DETAILED DESCRIPTION OF THE INVENTION

For the purpose of making objectives, features and advantages of the present disclosure clearer and more understandable, specific implementation modes of the present disclosure are described in detail below in combination with the accompanying drawings. Many specific details are specified in the following descriptions to facilitate full understandings of the present disclosure. However, the present disclosure may be implemented through many other modes different from those described herein. Those skilled in the art can make similar improvements without departing from contents of the present disclosure, thus the present disclosure will not be limited by the specific implementation disclosed below.

In the field of interventional therapy, generally, the end relatively close to an operator is called a proximal end, and the end relatively far away from the operator is called a distal end.

Unless otherwise defined, all technical and scientific terms used herein have the same meanings of general understandings of persons skilled in the art of the present disclosure. Terms used in the description of the present disclosure herein are only intended to describe the specific embodiments, but not to limit the present disclosure. Terms "and/or" used herein include any and all combinations of one or multiple relevant listed items.

Figure 2:
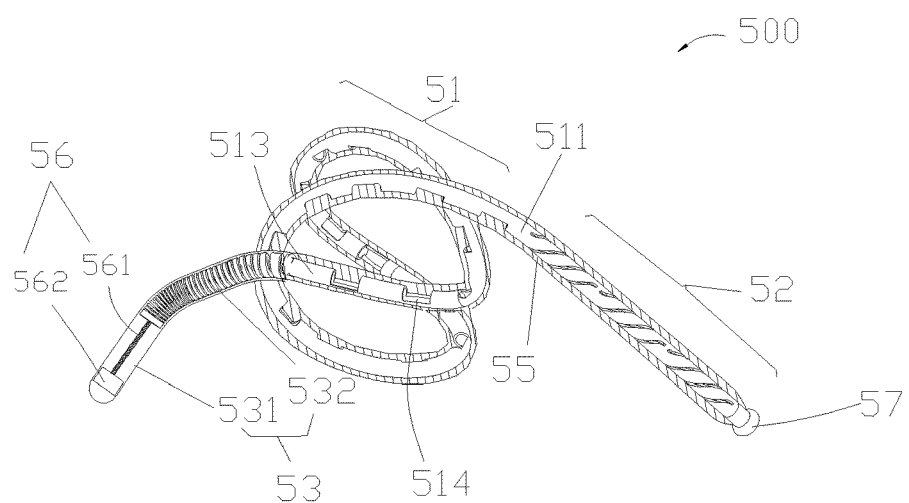
FIG. 2 is a schematic diagram of an implant provided by one embodiment of the present disclosure, with part of a thin film torn away.

Referring to FIG. 2, an elastic implant 500 provided by one embodiment of the present disclosure is of a tubular structure, including a hollow tubular elastic deformation part 51, a flexible guide part 53 connected to the distal end of the elastic deformation part 51, a connection part 52 connected to the proximal end of the elastic deformation part 51, a connection member 57 connected to the proximal end of the connection part 52, and an elastic thin film 55.

The flexible guide part 53 includes a first flexible section 531 and a second flexible section 532 connected between the first flexible section 531 and the elastic deformation part 51. The distal end of the first flexible section 531 serves as the distal end of the elastic implant 500. A radiograph component 56 is arranged in the first flexible section 531.

Figure 3:
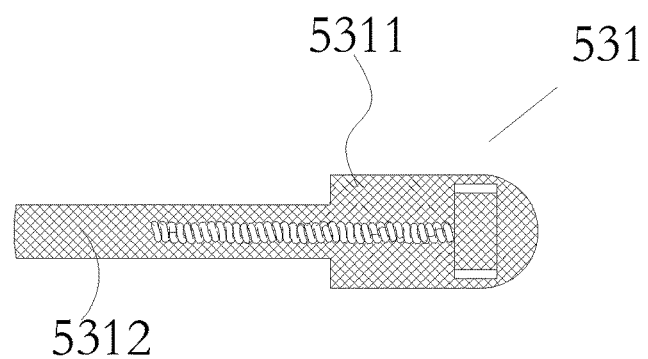
FIG. 3 is a structural schematic diagram of a first flexible section of the implant as shown in FIG. 2.

Referring also to FIG. 3, the first flexible section 531 includes an insert section 5312 and a distal section 5311. The part that is close to the proximal end of the implant 500 of the first flexible section 531 is the insert section 5312, and the part that is close to the distal end of the implant 500 of the first flexible section 531 is the distal section 5311. The insert section 5312 of the first flexible section 531 is inserted into the second flexible section 532. When the insert section 5312 of the first flexible section 531 is inserted into the second flexible section 532, the proximal end of the radiograph component 56 extends into the second flexible section 532. Specifically, the first flexible section 531 is made of a macromolecular elastic material, such as silica gel, polytetrafluoroethylene or a PEBAX material. The macromolecular elastic material is more flexible than a metal material and has a lower anti-bending force (the minimum force for bending the material), so that during implantation of the implant, the distal end that serves as the distal end of the implant 500 of the first flexible section 531 is the end in direct contact with tissue in a human body, so as to prevent the implant from bruising the tissue in the human body. Preferably, the distal-end face of the first flexible section 531 is designed to be a partial spherical face. During the implantation of the implant, when its distal end is in contact with the tissue, such as a bronchus or a lung, in the human body, the first flexible section 531 is easier to bend because of its characteristics of greater flexibility and lower anti-bending force, and therefore will not bruise the tissue in the human body.

The insert section 5312 and the distal section 5311 here may be formed in one piece. For example, they are directly manufactured through a mold or by a cutting method. The insert section and the distal section also may be separately manufactured and then fastened and connected through glue or other techniques, and there is no specific limitation here. The radial height of the insert section 5312 of the first flexible section 531 is less than that of the distal section 5311. In this manner, a joint of the insert section 5312 and the distal section 5311 can have a stepped shape. In the present embodiment, main body parts of the insert section 5312 and the distal section 5311 of the first flexible section 531 are preferably cylindrical, and the axial lines of the insert section 5312 and the distal section 5311 are located on the same horizontal line. The radial height of the insert section 5312 is matched with the inner diameter of the lumen of the second flexible section 532. When the first flexible section 531 is connected with the second flexible section 532, the insert section 5312 may be inserted into the lumen of the second flexible section 532. As the macromolecular material has a certain elasticity, the insert section 5312 may be properly compressed when inserted into the lumen of the second flexible section 532, and the elasticity of the material of the insert section 5312 may ensure that the insert section 5312 may be firmly fastened through the lumen of the second flexible section 532, thereby effectively avoiding the problem of ineffective connection reliability caused by other connection techniques. The radial height of the insert section 5312 being matched with the inner diameter of the lumen of the second flexible section 532 means that the radial height of the insert section 5312 may be slightly greater than, equal to, or less than the inner diameter of the lumen of the second flexible section 532. When the radial height is slightly greater than the inner diameter, the insert section 5312 is compressed to deform to squeeze into the lumen of the second flexible section 532, and may still be integrated with the second flexible section 532 without the help of a foreign object. When the radial height is equal to or less than the inner diameter, the insert section 5312 may be easily inserted into the lumen of the second flexible section 532, and at that moment, the insert section 5312 and the second flexible section 532 are connected into an unitary object with the help of the macromolecular elastic material covering the periphery of the second flexible section 532.

Preferably, the radial height of the distal section 5311 of the first flexible section 531 is equal to the outer diameter of the second flexible section 532. When the insert section 5312 of the first flexible section 531 is inserted into the lumen of the second flexible section 532, the width of the step of the joint of the insert section 5312 and the distal section 5311 may be equal to the thickness of the lumen wall of the second flexible section 532, so as to ensure that the outer surface of the joint of the first flexible section 531 and the second flexible section 532 is flush after the first flexible section 531 and the second flexible section 532 are connected, and then to guarantee the smooth outer surface of the implant to avoid injury to tissue organs in the human body caused by protrusions on the surface and also lower the subsequent processing difficulty. The second flexible section 532 is a tubular body cut from a nickel-titanium tube through laser and having cutting slots, and under the action of the same external force, its anti-bending performance from the distal end to the proximal end is gradually improved (that is, under the action of the same external force, the deformation performance from the distal end to the proximal end is gradually lowered, namely the second flexible section becomes harder from the distal end to the proximal end), so as to better guide the elastic implant 500. In addition, the anti-bending performance of the second flexible section 532 is lower than that of the elastic deformation part 51 and is higher than that of the first flexible section 531, so as to allow the flexible guide section 53 to move more effectively in the bronchus without injuring surrounding tissues.

It can be understood that, as the second flexible section 532 is the tubular body having the multiple cutting slots, the anti-bending performance of the second flexible section 532 may vary with the changes of the distances between adjacent cutting slots. Those skilled in the art can set the distances between adjacent cutting slots according to different clinical requirements to allow the anti-bending performance of the second flexible section 532 to be lower than that of the elastic deformation part 51.

The second flexible section 532 includes the continuously spiral cutting slots 2502. On a spread plane cut along the axial direction of the second flexible section 532, the distance between two adjacent cutting slots 2502 is also gradually increased from the distal end to the proximal end of the second flexible section 532 to gradually improve the anti-bending performance of the second flexible section 532 from the distal end to the proximal end.

It can be understood that, on the spread plane cut along the axial direction of the second flexible section 532, from the distal end to the proximal end of the second flexible section 532, when an included angle G between the extending direction 2505 of the cutting slots 2502 of the second flexible section 532 and the axial direction 2504 of the second flexible section 532 is unchanged, and the width of each cutting slot of the second flexible section 532 along the axial direction 2504 of the second flexible section 532 is gradually decreased, the distance between two adjacent cutting slots 2502 is gradually increased as well, so as to gradually improve the anti-bending performance of the second flexible section 532 from the distal end to the proximal end.

Figure 4:
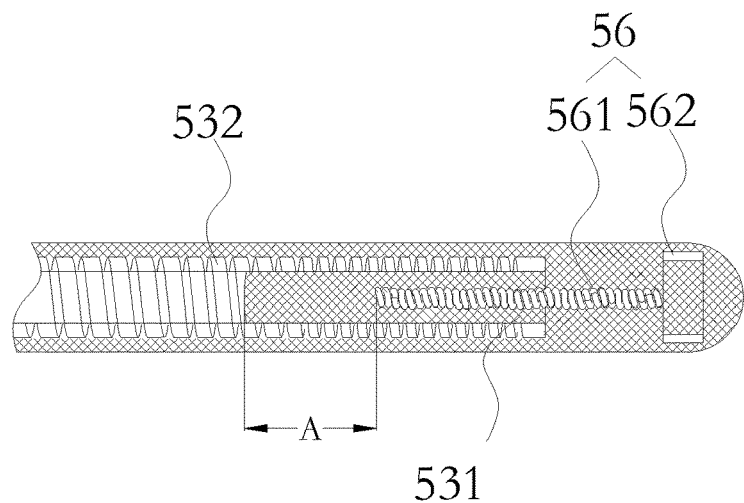
FIG. 4 is a partial sectional view of a flexible guide part of the implant as shown in FIG. 2.
Figure 5:
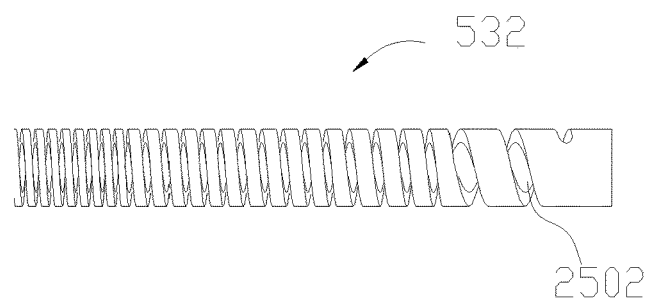
FIG. 5 is a structural schematic diagram of a second flexible section of the implant as shown in FIG. 2.
Figure 6:
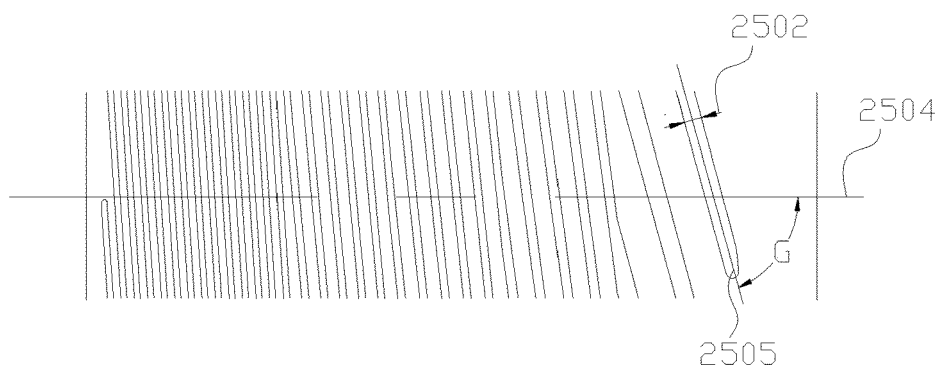
FIG. 6 is a schematic diagram of the second flexible section in FIG. 5 after it is cut along its longitudinal direction and spread apart.

It can be understood that, on the spread plane cut along the axial direction of the second flexible section 532, from the distal end to the proximal end of the second flexible section 532, when the width of each cutting slot of the second flexible section 532 along the axial direction 2504 of the second flexible section 532 is unchanged, and the included acute angle between the extending direction 2505 of the cutting slots of the second flexible section 532 and the axial direction 2504 of the second flexible section 532 is gradually increased, the distance between two adjacent cutting slots 2502 is gradually increased as well, so as to gradually improve the anti-bending performance of the second flexible section 532 from the distal end to the proximal end. It can be understood that, in other embodiments, the second flexible section 532 also may be omitted. At the moment, the insert section of the first flexible section 531 may be inserted into the elastic deformation part 51 as long as the distal section of the first flexible section 531 of the obtained implant is relatively flexible and does not injure the tissue easily. Referring to FIG. 4 again, the elastic radiograph component 56 is arranged in the first flexible section 531. As the first flexible section 531 is made of the macromolecular material, the radiograph component 56 may be embedded into the first flexible section 531, or may be arranged in the first flexible section 531 by other methods, and there is no specific limitation here. When the insert section of the first flexible section 531 is inserted into the lumen of the second flexible section 532, the proximal end of the radiograph component 56 extends into the lumen of the second flexible section 532. During the implantation of the implant 500, the implant 500 may be displayed through the radiograph component 56 in the first flexible section 531. In addition, as the proximal end of the radiograph component 56 extends into the lumen of the second flexible section 532, the radiograph component 56 may display a bending change of the first flexible section 531 and also may display a bending change of the second flexible section 532 during the implantation of the implant, so as to guarantee the accuracy and the safety of the operation. Furthermore, as the first flexible section 531 and the second flexible section 532 are made of different materials, the anti-bending force of the first flexible section 531 is lower than that of the second flexible section 532. When the implant twists a visceral organ or tissue, it is extremely easy to produce a dramatic deformation difference between the first flexible section 531 and the second flexible section 532, leading to relatively high stress concentration in a region having a relatively large deformation difference, and thus resulting in breakage between the first flexible section 531 and the second flexible section 532. However, the radiograph component 56 in the present embodiment may provide a certain stress support for the first flexible section 531 and the second flexible section 532 by virtue of its certain elasticity; that is, the anti-bending force difference between the first flexible section 531 and the second flexible section 532 may be reduced, so the flexible guide section is allowed to have a gradually changing anti-bending force, namely the anti-bending force is gradually lowered from the distal end to the proximal end to avoid the dramatic deformation difference between the flexible section 531 and the second flexible section 532 and thus avoid breakage between the first flexible section 531 and the second flexible section 532. Preferably, the proximal end of the radiograph component 56 is closer to the distal end of the implant 500 than the proximal end of the first flexible section 531, and a perpendicular distance A between the proximal end of the radiograph component 56 and the proximal end of the first flexible section 531 ranges between 0.5 mm and 20 mm. In the present embodiment, during the implantation, a core wire is required to be inserted into the lumen of the implant to restrain the elastic implant in an approximately linear delivery state, and the distal end portion of the core wire abuts with the outer wall of the proximal end of the first flexible section 531. The distance between the proximal end of the radiograph component 56 and the proximal end of the first flexible section 531 is 0.5 mm to 20 mm to ensure that the core wire does not touch the radiograph component 56 and further guarantee the firmness of the position of the radiograph component 56 in the first flexible section 531 so as to prevent the radiograph component 56 from being separated from the first flexible section 531 along with the pushing of the core wire. In addition, the perpendicular distance between the proximal end of the radiograph component 56 and the proximal end of the first flexible section 531 ranges between 0.5 mm and 20 mm to allow the clinical technician to adjust the entry depth of the radiograph component 56 in the second flexible section 532 based on the actual clinical situation, so as to allow the flexible guide section to have the gradually changing anti-bending force from the distal end to the proximal end, and avoid the breakage between the first flexible section 531 and the second flexible section 532. If the perpendicular distance between the proximal end of the radiograph component 56 and the proximal end of the first flexible section 531 is set to be less than 0.5 mm, the core wire can easily contact the radiograph component 56 during the implantation process, changing the shape of the radiograph component 56, thereby affecting the radiograph effect. If the perpendicular distance between the proximal end of the radiograph component 56 and the proximal end of the first flexible section 531 is set to be more than 20 mm, the gradually changing anti-bending force of the flexible guide section from the distal end to the proximal end would be greatly affected, and then the dramatic deformation difference between the first flexible section 531 and the second flexible section 532 would easily occur, so the possibility of breakage between the first flexible section 531 and the second flexible section 532 is increased. Referring to FIG. 2 and FIG. 4 together, the radiograph component 56 includes a radiograph wire 561 arranged in the longitudinal center axis direction of the first flexible section 531 and a radiograph ring 562 arranged at the distal end of the radiograph wire 561. The radiograph wire 561 has a certain length and may be made of a heavy metal material, such as gold, platinum and tungsten, which presents a relatively good radiographic effect under X-ray. Meanwhile, the radiograph wire 561 presents relatively good radiographic effect when bending along with the first flexible section 531 and the second flexible section 532, and the bending change of the radiograph wire 561 may reflect bending changes of the first flexible section 531 and the second flexible section 532 outside the radiograph wire 561. Preferably, the arrangement of the radiograph wire 561 in the longitudinal center axis direction of the first flexible section 531 will help to use the length of the radiograph wire 561 to the maximum extent, to ensure that it is maintained in an extending state in the first flexible section, and thereby achieve a better radiographic effect and provide a higher elasticity and a higher stress support to prevent the breakage between the first flexible section 531 and the second flexible section 532. In addition, as the instrument is required to be operated under the help of X-ray, the radiograph wire 561 is arranged in the first flexible section 531, and the proximal end extends into the second flexible section 532, to ensure that the bending degrees of the first flexible section 531 and the second flexible section 532 may be displayed during the implantation of the implant. When it is displayed that the first flexible section 531 bends to a certain extent, an operator can judge whether the end portion of the implant arrives at a predetermined position according to the displayed result, so as to improve the safety of the lung volume reduction surgery.

The radiograph ring 562 is close to the distal end of the first flexible section 531, and is preferably arranged at the distal end portion of the first flexible section 531. As the radiograph wire 561 is relatively thin, and the end portion of the first flexible section 531 is provided with the radiograph ring 562, the position information of the distal end of the implant may be effectively displayed during the implantation of the implant, so it is more favorable for the operator to judge the position of the distal end portion of the implant to improve the safety and the accuracy of the operation.

It can be understood that, in other embodiments, the radiograph wire of the radiograph component 56 may include a core shaft and a radiographic material arranged on the core shaft. The radiographic material is preferably a heavy metal material, such as gold, platinum and tungsten, which provides relatively good radiograph effect under X-ray. The core shaft is preferably made of a nickel-titanium alloy, a cobalt-chromium alloy and the like which is relatively high in elasticity. This design mode also ensures that the radiograph component 56 has high elasticity. It can be further understood that, in other embodiments, the radiograph ring 562 in the radiograph component 56 may be omitted depending on actual clinical requirements.

The elastic deformation part 51 with superelasticity includes a proximal end 511 and a distal end 513 which are opposite to each other. The distal end 513 is connected with the flexible guide part 53. The elastic deformation part 51 further includes multiple mutually isolated cutting slots 514 communicating with the lumen of the elastic deformation part 51. The multiple cutting slots 514 allow the elastic deformation part 51 of the elastic implant 500 to bend into a predetermined shape in the natural state, such as a shape as shown in FIG. 2.

The elastic deformation part 51 is of a predetermined curled shape in its natural state (in the absence of an external force), and may be restrained into a straight bar shape or any other shapes under the action of an external force and recovers to the predetermined shape through bending and torsion after the external force is withdrawn. The elastic deformation part 51 may be made of a material commonly used in the industry and having superelasticity. In the present disclosure, there is no limitation to specific materials as long as this material is can be used in the human body and has superelasticity. In the present embodiment, the elastic deformation part 51 is made of a nickel-titanium alloy. Specifically, a processing method of the elastic deformation part 51 includes: first, a section of hollow nickel-titanium tube having a diameter of about 0.5 mm to 2.0 mm and a wall thickness of 0.01 mm to 0.4 mm is cut by laser; second, the cut nickel-titanium tube is bent into a shape as shown by the elastic deformation part 51 in FIG. 2 through a mold; and finally, the tube is thermally set to form the elastic deformation part 51.

Figure 8:
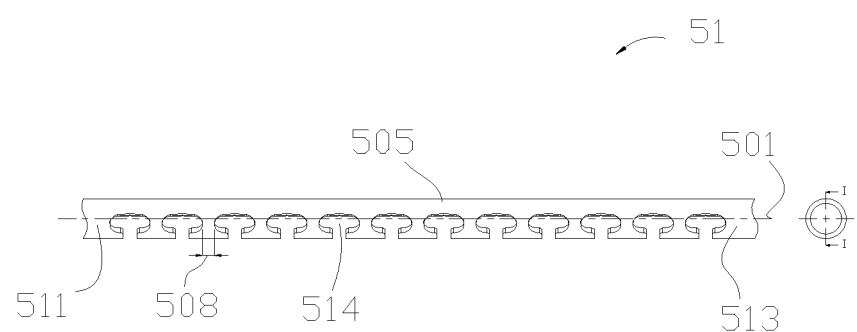
FIG. 8 is a sectional view of an elastic deformation part of the implant as shown in FIG. 2.
Figure 9:
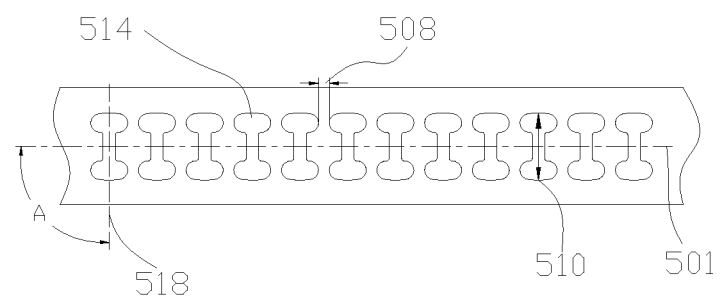
FIG. 9 is a schematic diagram of the cutting slots of the elastic deformation part of the implant in FIG. 2 after the elastic deformation part is cut along its longitudinal direction and spread apart.

Referring together to FIGS. 8 and 9, in the present embodiment, to allow the elastic deformation part 51 to extend into a thinner bronchus and to achieve a better squeezing effect on corresponding tissues, preferably, a conical nickel-titanium tube having a consistent inner diameter and a gradually changing wall thickness is adopted, such as a conical nickel-titanium tube having an inner diameter of 0.8 mm to 1.0 mm and the wall thickness varying from 0.01 mm at the distal end to 0.4 mm at the proximal end. Multiple dumbbell-shaped cutting slots 514 are formed in the nickel-titanium tube. The extending direction (namely the direction of the incision) 518 of these cutting slots 514 and the axial line 501 of the elastic deformation part 51 form a certain angle A. Preferably, the angle A is 10 to 90 degrees. A gap 508 of about 0.05 mm to 0.5 mm is provided between two adjacent cutting slots 514. It can be understood that, as the elastic deformation part 51 has the multiple cutting slots 514, the anti-bending performance of the elastic deformation part 51 may vary with the changes of the lengths 510 of the cutting slots 514 in the extending direction 518. Those skilled in the art can set the lengths 510 of the cutting slots 514 of the elastic deformation part 51 in the extending direction 518 according to an actual clinical requirement to allow the anti-bending performance of the flexible guide part 53 to be lower than that of the elastic deformation part 51.

Figure 10:
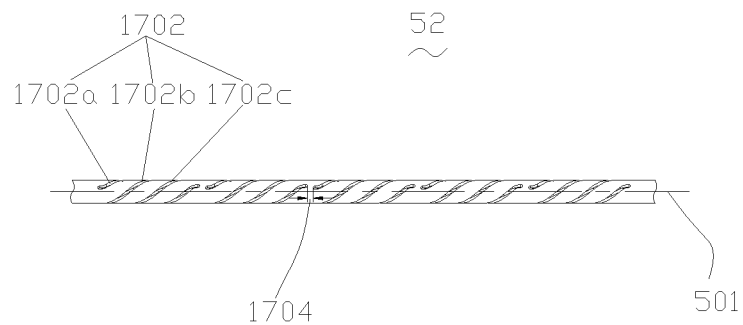
FIG. 10 is a schematic diagram of a connection part of the implant in FIG. 2.
Figure 11:
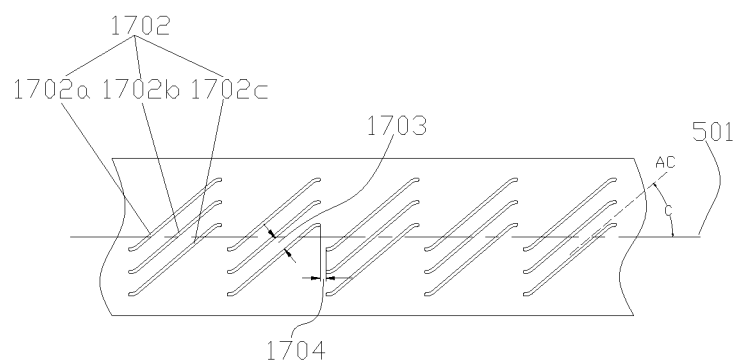
FIG. 11 is a schematic diagram of the connection part in FIG. 10 after the connection part is cut along its longitudinal direction and spread apart.

Referring together to FIGS. 10 and 11, the connection part 52 is connected between the connection member 57 and the elastic deformation part 51. Under the action of the same external force, the anti-bending performance of the connection part 52 is lower than that of the elastic deformation part 51 (namely, under the action of the same external force, the connection part 52 deforms more easily than the elastic deformation part 51). In the present embodiment, the connection part 52 is provided with multiple cutting slot groups 1702. After the connection part 52 is cut along the axial direction and spread out, it can be seen that each cutting slot group 1702 includes three cutting slots 1702a, 1702b and 1702c arrayed along the circumferential direction of the connection part 52 and parallel to one another. The two ends of the three cutting slots are aligned with each other in the circumferential direction. A certain gap 1703 is provided between two adjacent cutting slots in each cutting slot group 1702, and a gap 1704 is provided between two adjacent cutting slot groups 1702. Each cutting slot has a slim structure, and the extending direction AC of the multiple cutting slots and the axial line 513 of the connection part 52 form a certain included angle C. By adjusting the number of the cutting slots in each cutting slot group 1702, the size of each gap 1703, the size of the included angle C between the extending direction AC of the cutting slots and the axial line 501 of the elastic deformation part 51, and the size of the gap 1704 between two adjacent cutting slot groups 1702, the anti-bending performance of the entire connection part 52 can be adjusted to be lower than that of the elastic deformation part 51. In other embodiments, each cutting slot group 1702 may include 2 to 6 cutting slots, the gap 1703 between two adjacent cutting slots in each cutting slot group 1702 is 0.05 mm to 1 mm, the included angle C is 10 to 85 degrees, and the gap 208 between two groups is 0.1 mm to 1.0 mm. The elastic deformation part 51 has an outer diameter of about 1.0 mm to 2.0 mm and a wall thickness of 0.05 mm to 0.3 mm. The connection between the connection part 52 and the elastic deformation part 51 may be implemented by techniques such as covering of a macromolecular thermal shrinkage tube or thin film, gluing, laser welding, soldering and the like. Based on the prior art, integrated cutting is preferred, and the elastic deformation part 51 and the connection part 52 which have different textural features are cut from different areas on the same tube.

It can be understood that, in other embodiments, the cutting slots and the lumen may also not be connected as long as the elasticity of the elastic deformation part is improved. It can be further understood that, in other embodiments, the characteristic of the gradually improving anti-bending performance of the elastic deformation part from the distal end to the proximal end may also be accomplished in other ways. For example, a tube body, the wall thickness of which is gradually increased from the distal end to the proximal end, can be adopted.

Figure 12:
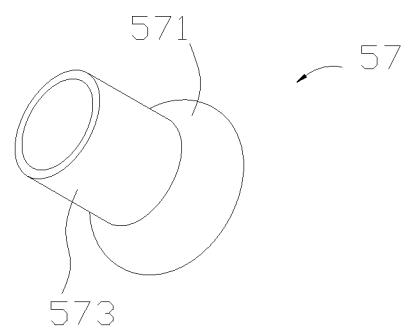
FIG. 12 is a schematic diagram of a connection member of the implant in FIG. 2.
Figure 13:
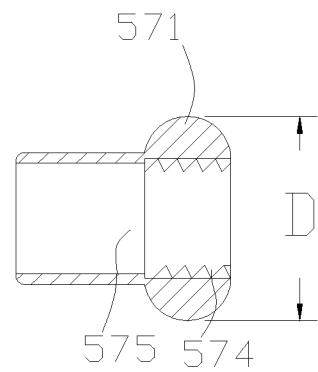
FIG. 13 is a sectional view of the connection member in FIG. 12.

Referring together to FIGS. 2, 12 and 13, the connection member 57 is located at the proximal end of the connection part 52 and includes a boss 571 and a connection section 573. The outer diameter D of the boss 571 is greater than the outer diameter of the part of the elastic implant 500 that is close to the boss 571 in a delivery state. In the present implementation mode, the outer diameter of the part of the elastic implant 500 that is close to the boss 571 in the delivery state is the outer diameter of the proximal end of the connection part 52. An internal thread 574 is arranged inside the boss 571. The connection section 573 is located between the boss 571 and the connection part 52, and is provided with a cavity 575 extending through the proximal-end face and the distal-end face of the connection section 573. In the present embodiment, the cross section that is parallel to the longitudinal center axis of the boss 571 includes two opposite semi-circles. The outer diameter D may not exceed 2.8 mm and is preferably 2.0 mm to 2.3 mm. The boss 571 effectively enlarges a contact area of the proximal end of the elastic implant 500 with the bronchus to reduce the injury to the lung tissues after the elastic implant 500 has been implanted.

Figure 14:
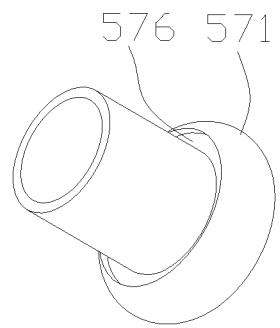
FIG. 14 is a schematic diagram of deformation of the connection member in FIG. 12.
Figure 15:
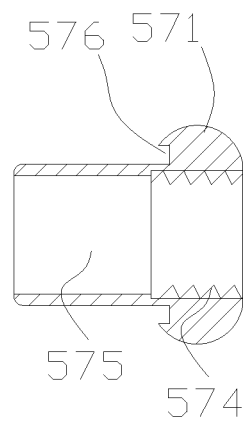
FIG. 15 is a sectional view of the connection member in FIG. 14.

It can be understood that part of the distal-end face of the boss 571 may also be sunken towards the proximal end of the boss 571 to form an annular groove 576 (see FIGS. 14 and 15) surrounding the longitudinal center line of the boss 571, so as to provide a fastening position for biopsy forceps, so that the biopsy forceps can clamp a connection apparatus more effectively to withdraw the elastic implant 50.

Figure 7:
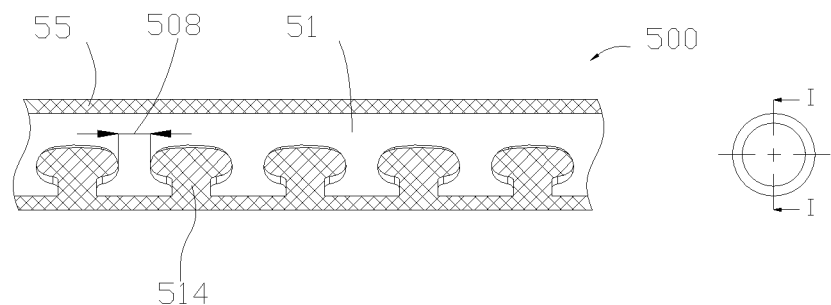
FIG. 7 is a partial sectional view of the implant in FIG. 2.

Referring together to FIGS. 2 and 7, the elastic implant thin film 55 completely covers the outer surface of the elastic implant 500 except the boss 571 and fills each cutting slot 514 without blocking the lumen of the elastic implant 500, thereby ensuring that the elastic implant thin film 55 firmly covers the elastic implant 500 and guarantees no blockage in the lumen of the elastic implant 500. The elastic implant thin film 55 may have a thickness of 0.01 mm to 0.8 mm. The elastic implant thin film 55 may be made of a macromolecular solution featured by good chemical stability, water resistance and weathering resistance, low compressibility, good biocompatibility, high mechanical strength, nontoxicity, being odorless, and the like. For example, these macromolecular solutions may be silicone rubber or polyurethane solutions. As the first flexible section 531 is also made of the macromolecular material, and the insert section of the first flexible section 531 is inserted into the lumen of the second flexible section 532, when the elastic implant thin film 55 covers the surface of the elastic implant, the periphery of the second flexible section 532 is completely covered by the macromolecular material, which allows the second flexible section 532 and the first flexible section 531 to be combined more securely and allows the connection between the elastic implant thin film 55 and the implant to be more stable. It is easiest for the proximal end portion of the elastic implant thin film 55 to roll over and fall off under the action of an external force due to the combination characteristic of the elastic implant thin film 55 and a metal matrix, but the outer diameter of the boss 571 is greater than that of the part of the elastic implant 500 that is close to the boss 571 in the delivery state, so the boss 571 can protect the proximal end portion of the elastic implant thin film 55 from being in contact with a vascular wall during the delivery and withdrawal processes, and thereby protect the elastic implant thin film 55 from rolling over and falling off during the delivery and withdrawal processes.

Figure 16:
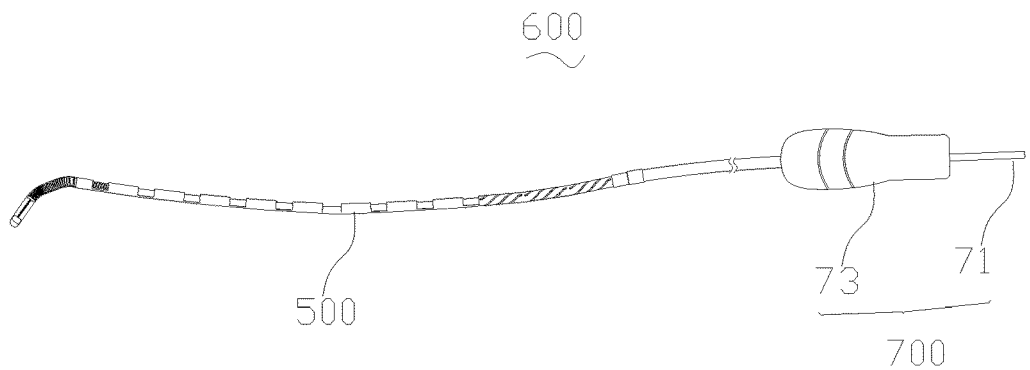
FIG. 16 is a schematic diagram of a lung volume reduction instrument provided by one embodiment of the present disclosure.
Figure 17:
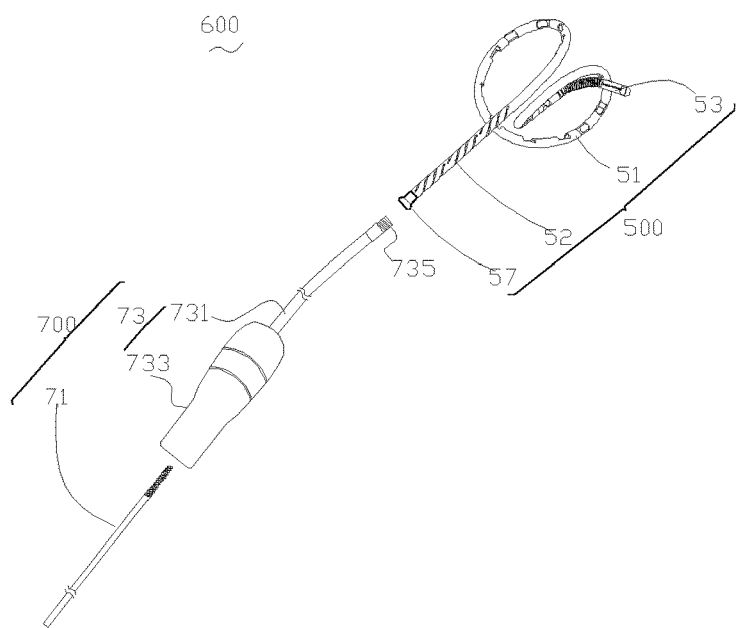
FIG. 17 is an exploded schematic diagram of the lung volume reduction instrument in FIG. 16.

Referring together to FIGS. 16 and 17, a lung volume reduction instrument 600 provided by one embodiment of the present disclosure includes an elastic implant 500 and a delivery apparatus 700. The delivery apparatus 700 includes a core wire 71 and a pushing mechanism 73.

The core wire 71 is accommodated in the lumen of the elastic implant 500 to restrain the elastic implant 500 into an approximately linear delivery state to conveniently deliver the implant 500 to a lesion locus. The core wire 71 may be made of a section of metal wire having a diameter of 0.1 mm to 1.1 mm.

Figure 18:
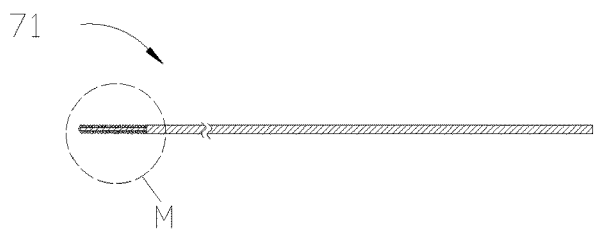
FIG. 18 is a schematic diagram of a core wire of the lung volume reduction instrument in FIG. 16.
Figure 19:
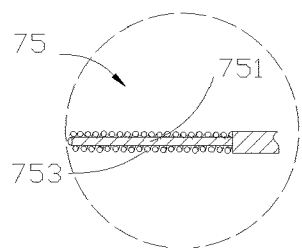
FIG. 19 is an enlarged view of the part M of FIG. 18.
Figure 20:
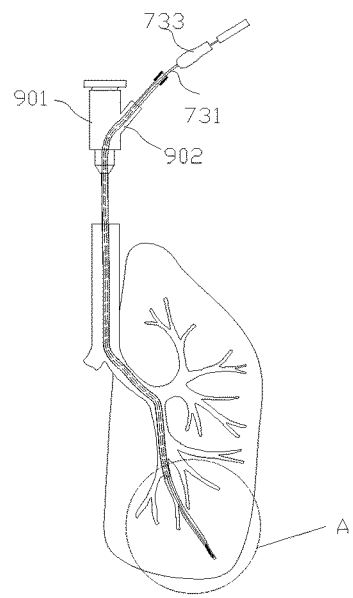
FIG. 20 is a schematic diagram of a working channel built by a lung volume reduction instrument provided by one embodiment of the present disclosure.
Figure 21:
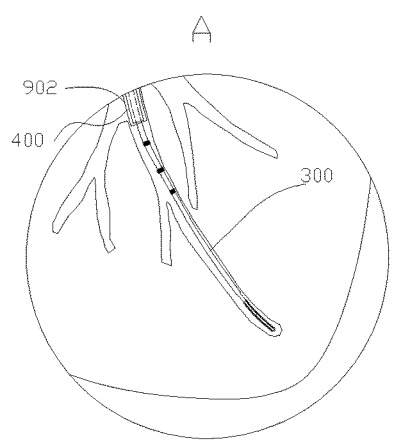
FIG. 21 is an enlarged view of the part A of FIG. 20.
Figure 22:
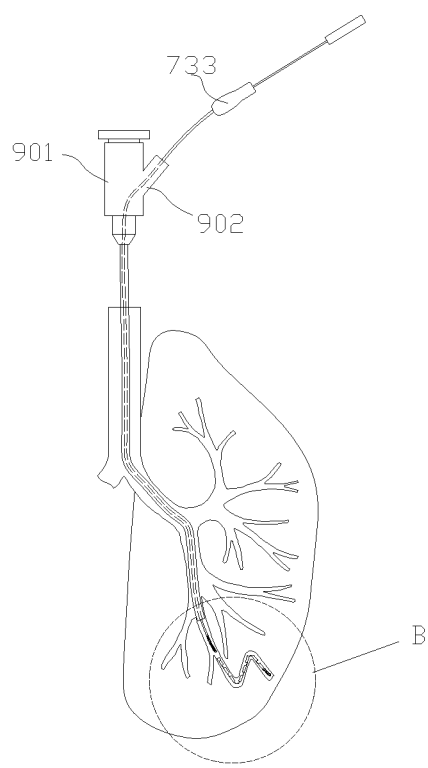
FIG. 22 is a schematic diagram after the implant is released.
Figure 23:
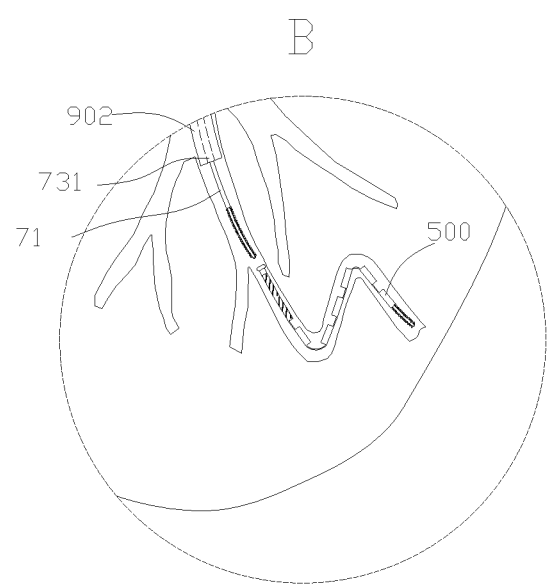
FIG. 23 is an enlarged view of the part B of FIG. 22.

Referring together to FIGS. 18 and 19, for the purpose of safe and convenient operation, a flexible core wire guide head 75 coaxial with the core wire 71 and provided with a radiopaque marker is required to be arranged at the distal end of the core wire 71. The outer diameter of the core wire guide head 75 is consistent with that of the core wire 71. The core wire guide head 75 includes a guide column 751 and a spring 753 fixedly arranged outside ad surrounding the guide column 751. The guide column 751 and the core wire 71 can be provided in one piece, or the guide column 751 is fixedly connected to the distal end of the core wire 71. The spring 753 is provided with a radiopaque marker.

The core wire guide head 75 is used for guiding the core wire 71 to successfully enter the lumen of the elastic implant 500. The flexible core wire guide head 75 may be implemented using a soft spring, that is, the spring 753 is arranged on the guide column 751 which is provided in one piece with the core wire 71, or fixedly connected to and surrounding the distal end of the core wire 71. A specific manufacturing method is as follows: first, the head end of the core wire 71 is thinned to prepare the guide column 751, and then one section of spring 753 having a length of 5 mm to 150 mm is fixed outside the guide column 751. The spring 753 may be fixed on the core wire 71 using techniques such as covering of a macromolecular thermal shrinkage tube or thin film, gluing, laser welding, soldering and the like. Under the guidance of the flexible core wire guide head 75, the core wire 71 may successfully enter the lumen of the implant 500 from the proximal end of the implant 500 and may restrain the implant 500 from the shape as shown in FIG. 2 into the approximately linear shape (as shown in FIG. 16).

In the present embodiment, due to the existence of the flexible guide part 53, the implant 500 loaded with the core wire 71 also has the effect of exploring a pathway in the bronchus to the lesion region. To guide and monitor the operation condition of the core wire 71 entering the lung, the radiopaque marker is required to be arranged on the core wire guide head 75. The radiopaque marker can display the implant through a fluorescent inspection system, an ultrasonic imaging system, an MRI (Magnetic Resonance Imaging) system, a computed tomography (CT) system or other remote imaging systems. There is no limitation to specific systems. The core wire 101 is displayed and guided through these systems. In the present embodiment, the spring wound by a metal wire, such as a tungsten metal wire or a tantalum metal wire, having relatively high X-ray radiograph performance and a wire diameter of 0.01 mm to 0.3 mm, serves as the radiopaque marker. In the present embodiment, the radiopaque marker and the core wire guide head 75 are combined into one component to realize two functions. In addition to this mode, an additional radiopaque marker can also be arranged on the core wire guide head 75. Of course, when the surface of the implant of the present disclosure is not covered by an elastic film and the implant itself is made of a radiographic material such as a nickel-titanium alloy, the radiopaque marker may be omitted.

Referring again to FIG. 17, the pushing mechanism 73 includes a delivery mechanism 731 and an operation handle 733 connected with the delivery mechanism 731. The delivery mechanism 731 and the implant 500 surround the core wire 71, and the distal end of the delivery mechanism 731 is detachably connected with the proximal end 511 of the implant 500. In the present embodiment, the delivery mechanism 731 is a pushing steel cable, and its distal end is provided with a connection matching part 735 having an external thread matched with the internal thread of the connection member 57. During assembly, the internal thread of the connection member 57 may be in threaded connection with the connection matching part 735 through the external thread of the pushing mechanism 73, and the implant 500 can be reliably fixed at the distal end of the delivery mechanism 73. After the implant 500 is pushed to a corresponding position of the bronchus, the connection member 57 of the implant 500 and the connection matching part 735 of the delivery mechanism 73 are unscrewed and separated by turning around the operation handle 733 of the pushing mechanism 73. The connection member 57 and the connection matching part 735 can also be other detachable fixed connection components, such as a magnetic connection apparatus, an elastic buckle or a noose, which are respectively arranged on the implant 500 and the delivery mechanism 103 to accomplish a detachable connection.

The elastic implant 500, the core wire 71 and the delivery mechanism 731 are assembled as follows: first, the elastic implant 500 is in threaded connection with the connection matching part 735 at the distal end of the delivery mechanism 731 to allow the delivery mechanism 731 to communicate with an internal channel of the elastic implant 500; and then the core wire 71 is pushed into the elastic implant 500 along the channel of the delivery mechanism 731 to restrain the curled elastic implant 500 in its natural state into a tube that is in an approximately linear delivery state.

Referring to FIGS. 20 to 23, a delivery catheter 400 is pushed to the distal end of a working channel 902 along the working channel 902 of a bronchoscope 901; a measurement guide wire 300 enters the delivery catheter 400, and extends out of the delivery catheter 400 to enter the bronchus; the delivery catheter 400 is pushed along the measurement guide wire 300 until the distal end of the delivery catheter 400 is overlapped with the distal end of the measurement guide wire 300; while maintaining the position of the delivery catheter 400 unchanged, the measurement guide wire 300 is withdrawn until it is completely withdrawn out of the delivery catheter 400; the elastic implant 500 installed with the delivery mechanism 731 is pushed along an inner cavity of the delivery catheter 400 until it can be seen under X-ray that the distal end of the elastic implant 500 is overlapped with the distal end of the delivery catheter 400; the operation handle 733 is operated to withdraw the core wire 71 from the elastic implant; along with the withdrawal of the core wire 71, the elastic implant 500 automatically recovers its natural shape from the straight bar-shaped delivery state restrained by the core wire 71, and can squeeze and pull the emphysema region in this recovery process, and also allow relatively healthy peripheral lung tissues to better exert their respiratory physiological functions to achieve a lung volume reduction effect; and the elastic implant 500 is released by operating the operation handle 733.

Figure 24:
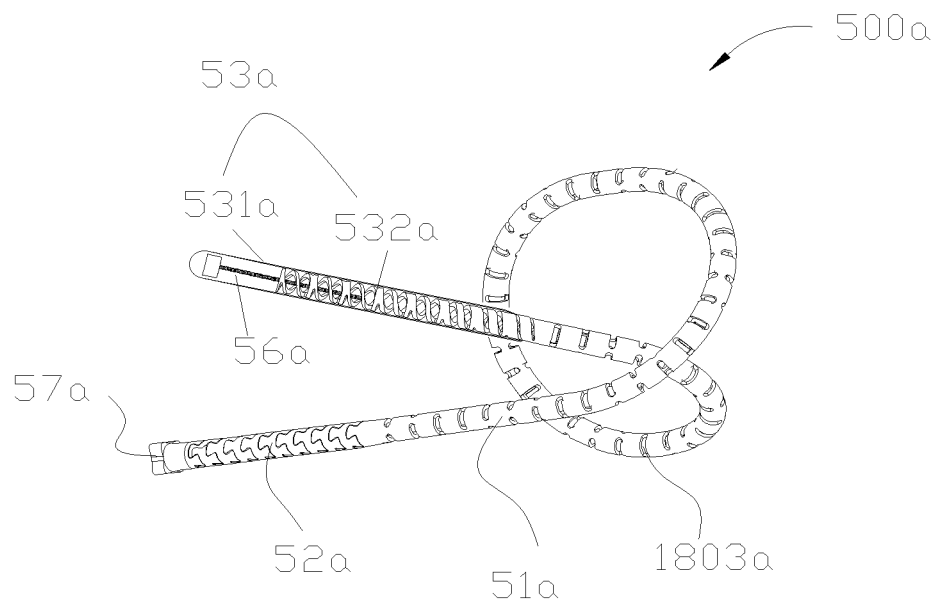
FIG. 24 is a schematic diagram of an implant provided by another embodiment of the present disclosure.

Referring to FIG. 24, an elastic implant 500a provided by another embodiment of the present disclosure has a tubular structure and includes an elastic deformation part 51a, a flexible guide part 53a connected with the distal end of the elastic deformation part 51a, a connection part 52a connected with the proximal end of the elastic deformation part 51a, a connection member 57a connected with the proximal end of the connection part 52a, and an elastic thin film 55a. The flexible guide part 53a includes a first flexible section 531a and a second flexible section 532a connected between the first flexible section 531a and the elastic deformation part 51a. The distal end of the first flexible section 531a serves as the distal end of the elastic implant 500a. A radiograph component 56a is arranged in the first flexible section 531a.

The structures of the first flexible section 531a and the first flexible section 531 are substantially the same, and the structures of the radiograph component 56a and the radiograph component 56 are approximately the same, so no more details will be described here.

Figure 25:
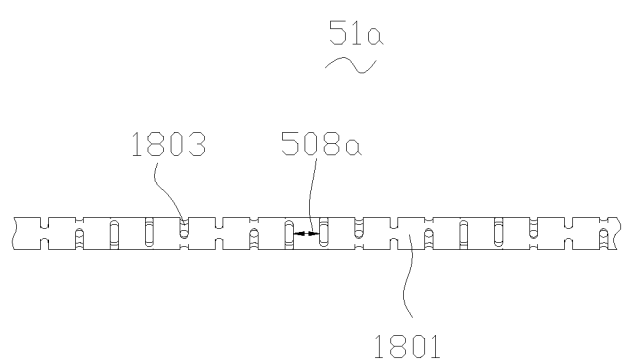
FIG. 25 is a schematic diagram of an elastic deformation part of the implant in FIG. 24.
Figure 26:
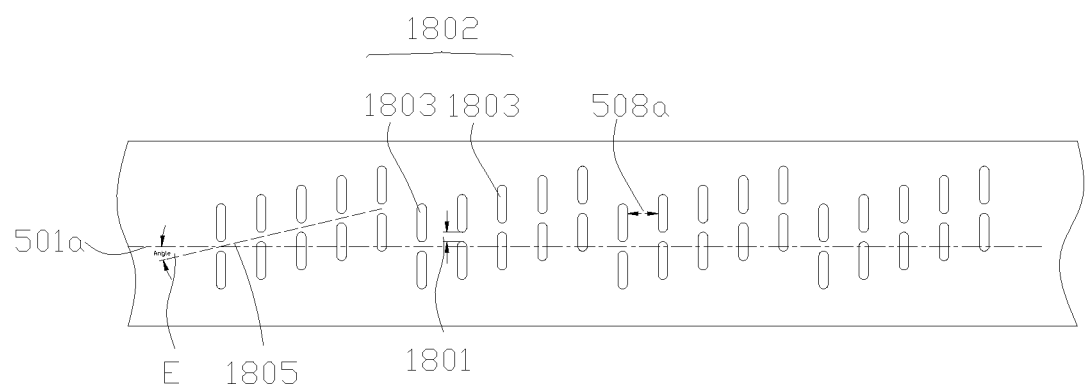
FIG. 26 is a schematic diagram of the elastic deformation part in FIG. 24 after the elastic deformation part is cut along its longitudinal direction and spread apart.

Referring together to FIGS. 25 and 26, the elastic deformation part 51a includes multiple cutting slot clusters 1802 arrayed in a spaced-apart manner along an axial direction of the elastic deformation part 51a. Each cutting slot cluster 1802 is composed of five side-by-side elliptical cutting slot groups 1803 arrayed in a step-like manner. In the present embodiment, each cutting slot group 1803 is composed of two paratactic cutting slots. A certain distance 1801 is provided between the two cutting slots in each cutting slot group 1803. The long axis of each cutting slot is perpendicular to the axial line of the elastic deformation part 51a. An extending direction 1805 of the arrangement between one group and another group in each cutting slot cluster 1802 and the axial line 501a of the elastic deformation part 51a form a certain included angle E which may be 60 to 90 degrees. A distance 508a of about 0.3 mm to 5 mm is provided between two adjacent cutting slot groups 1803 in each cutting slot cluster 1802. The step-like arrayed cutting slot groups 1803 are favorable for bending the elastic deformation part 51a into a specific shape. A part, having a length of about 0.5 mm to 5 mm, of the proximal end 511a of the elastic deformation part 51a is cut into a threaded trench serving as a connection member 57a. The cut nickel-titanium tube is bent into a shape as shown in FIG. 24 with a mold and then is thermally set into the elastic deformation part 51a of the elastic implant 500a.

Figure 27:
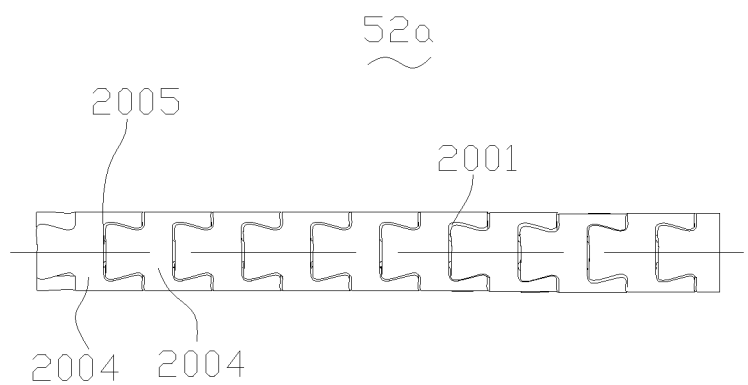
FIG. 27 is a schematic diagram of a connection part of the implant in FIG. 24.
Figure 28:
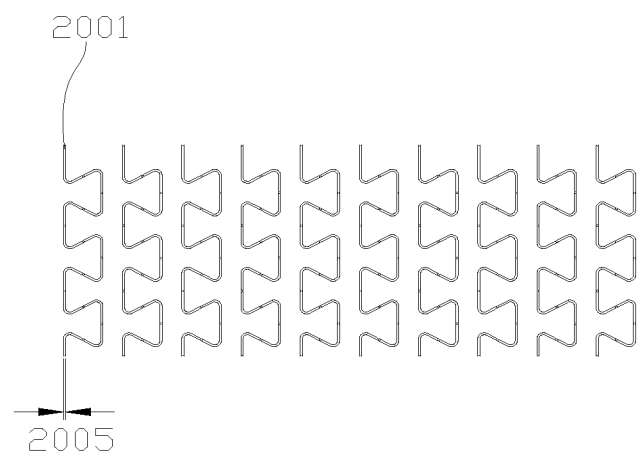
FIG. 28 is a schematic diagram of the connection part in FIG. 27 after the connection part is cut along its longitudinal direction and spread apart.
Figure 29:
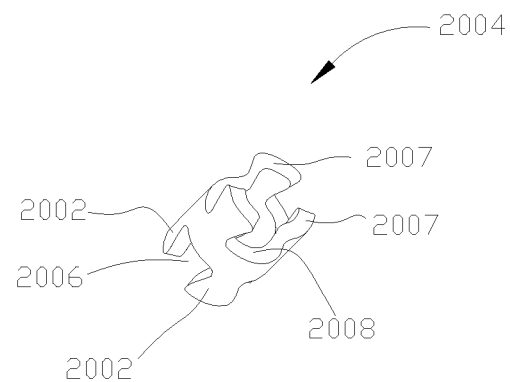
FIG. 29 is a schematic diagram of a connection sub component of the connection part in FIG. 27.

Under the action of the same external force, the anti-bending performance of the connection part 52a is lower than that of the elastic deformation part 51a so as to better reduce the injury of the connection part 52a to the wall of the bronchus. Referring to FIGS. 27 to 29, in the present embodiment, the connection part 52a is a tubular body formed by connecting multiple hollow sub components 2004 end-to-end and having multiple circumferentially continuous wave-shaped cutting slots 2001. Each cutting slot 2001 has a certain width 2005. Preferably, the width of each cutting slot may be 0.01 mm to 0.3 mm. The start point and the end point of two adjacent wave-shaped cutting slots 2001 are overlapped in the circumferential direction of the connection part 52a. Preferably, in the present embodiment, the proximal end of each sub component 2004 includes multiple proximal end protrusions 2002 distributed in an equal spaced-apart manner along the circumferential direction of the hollow sub component 2004. The circumferential length of each proximal end protrusion 2002 from the proximal end to the distal end is gradually decreased, so a dovetail-shaped proximal end groove 2006 having an opening facing the proximal end is formed between two adjacent proximal end protrusions 2002. The distal end of each hollow sub component 2004 includes multiple distal end protrusions 2007 distributed in an equal spaced-apart manner along the circumferential direction of the hollow sub component 2004. The circumferential length of each distal end protrusion 2007 from the proximal end to the distal end is gradually increased, so a dovetail-shaped distal end groove 2008 having an opening facing the distal end is formed between two adjacent distal end protrusions 2007. The number of the proximal end protrusions 2002 of each hollow sub component 2004 is equal to that of the distal end protrusions 2007 of the same hollow sub component 2004, and one distal end groove 2008 on each hollow sub component 2004 is aligned with one proximal end protrusion 2002 on the same hollow sub component 2004. In this way, in two hollow sub components 2004, the multiple dovetail-shaped proximal end protrusions 2002 on one hollow sub component 2004 mesh with the multiple distal end grooves 2008 of the other hollow sub component 2004, so that the two mutually-separated hollow sub components 2004 form an interlocked structure, and the multiple hollow sub components 2004 are spliced and combined into the connection part 52a. As all the mutually separated hollow sub components 2004 are connected through meshing structures of the dovetail-shaped protrusions and the dovetail grooves, the connection part 52a of this structure has extremely high flexibility and extremely high connection strength, and can transmit a torsion to the elastic deformation part 51a in a ratio of 1:1 during twisting of the connection member 57. Based on the prior art, the sub components 2004 can also be made by other techniques such as machining, casting and powder metallurgy. It can be understood that the connection part 52a is extremely high in flexibility and extremely low in anti-bending performance, so it is very easy to make the anti-bending performance of the connection part 52a lower than that of the elastic deformation part 51a by adjusting the anti-bending performance of the elastic deformation part 51a. It can be understood that the multiple proximal end protrusions 2002 can also be distributed at the proximal end of the sub component 2004 in a non-equal spaced-apart manner as long as the multiple sub components 2004 can be spliced.

Under the action of the same external force, the anti-bending performance of the flexible guide part 53a is lower than that of the elastic deformation part 51a so as to better guide the elastic deformation part 51a to move in the bronchus and reduce the injury to the wall of the bronchus. Under the action of the same external force, the anti-bending performance of the second flexible section 53a from the distal end to the proximal end is gradually improved.

Figure 30:
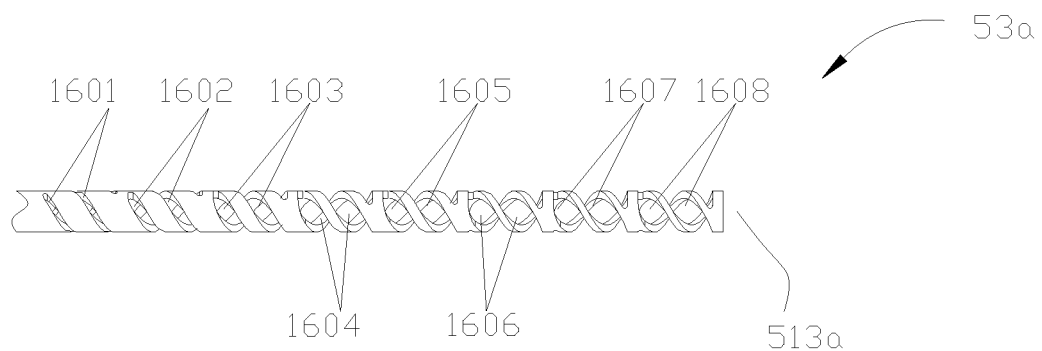
FIG. 30 is a schematic diagram of a flexible guide part of the implant in FIG. 24.
Figure 31:
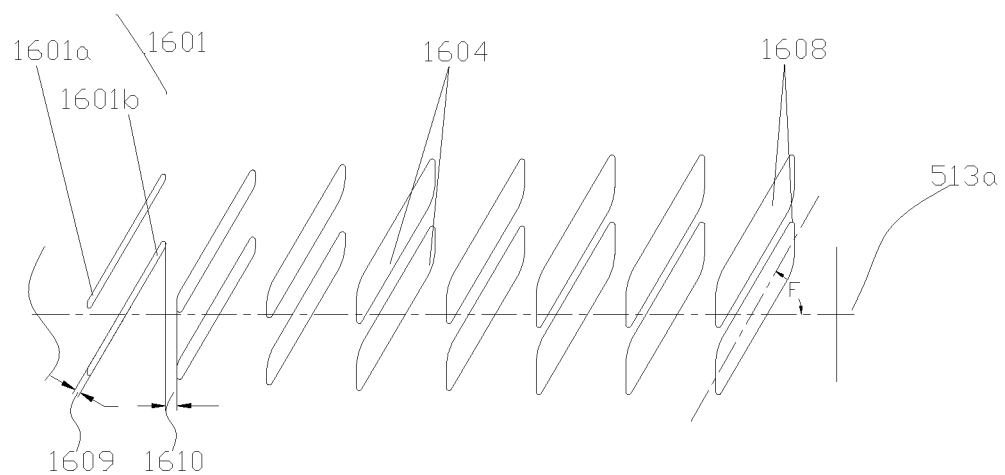
FIG. 31 is a partial schematic diagram of the flexible guide part in FIG. 30 after the flexible guide part is cut along its longitudinal direction and spread apart.

Referring together to FIGS. 30 and 31, in the present embodiment, the second flexible section 532a is a tubular body laser cut from a nickel-titanium tube and has cutting slots, and under the action of the same external force, the anti-bending performance of the second flexible section 532a from the distal end to the proximal end is gradually improved (that is, under the action of the same external force, the deformation performance of the second flexible section 532a from the distal end to the proximal end is gradually lowered; namely, the second flexible section 532a becomes gradually harder from the distal end to the proximal end) so as to better guide the elastic implant 500. It can be understood that as the second flexible section 532a is the tubular body having the multiple cutting slots, the anti-bending performance of the second flexible section 532a may vary with changes in the distances between adjacent cutting slots. Those skilled in the art can set the distances between adjacent cutting slots according to an actual clinical requirement to allow the anti-bending performance of the second flexible section 532a to be lower than that of the elastic deformation part 51a.

The second flexible section 532a includes multiple slender cutting slot groups 1601-1608. Each cutting slot group (such as 1601) is composed of two or more parallel cutting slots 1601a and 1601b, and each parallel cutting slot has a certain width 1609. The extending direction of these cutting slot groups 1601-1608 and the axial line 513a of the flexible guide part 53a form a certain angle F. A gap 1610 is provided between two adjacent cutting slot groups. By adjusting the number and the widths 1609 of the cutting slots in each cutting slot group, the size of the angle F and the size of each gap 1610, the anti-bending performance of the second flexible section 532a can be adjusted. Preferably, there may be 2 to 6 parallel cutting slots 1601, the width 1609 may be 0.05 mm to 1 mm, the angle F is preferably 5 to 85 degrees, and the gap 1610 is preferably 0.1 mm to 1.0 mm. The parallel cutting slot groups (1601-1608) having different widths 1609 are combined into the same nickel-titanium tube to fulfill the objective of gradually improving the anti-bending performance of the second flexible section 532a from the distal end to the proximal end under the action of the same external force. The flexible guide section 53a having the gradually changing anti-bending performance can better guide the elastic implant 500a.

The connection between the second flexible section 532a and the elastic deformation part 51a may be implemented through techniques such as covering of a macromolecular thermal shrinkage tube or thin film, gluing, laser welding, soldering and the like. Based on the prior art, integrated cutting is preferred, and the second flexible section 532a and the elastic deformation part 51a which have different textural features are cut from different areas on the same tube. To achieve the gradually changing anti-bending performance of the flexible guide section 53a, one feasible mode is to keep the angle F in two adjacent cutting slot groups unchanged and gradually decrease the width 1609 of each cutting slot from the distal end to the proximal end, and another feasible mode is to keep the width 1609 of each cutting slot in two adjacent cutting slot groups unchanged and gradually increase the angle F from the distal end to the proximal end. It can be understood that simultaneously changing the angle F and the width 1609 of each cutting slot in two adjacent cutting slot groups can also achieve the effect of gradually improving the anti-bending performance of the flexible guide section 53a from the distal end to the proximal end.

Figure 32:
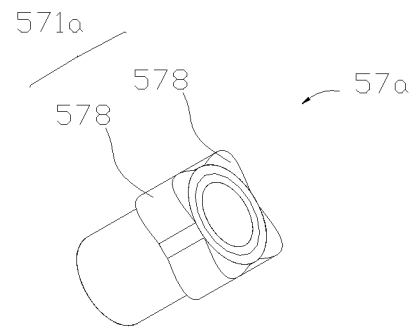
FIG. 32 is a schematic diagram of a connection member of the implant in FIG. 24.
Figure 33:
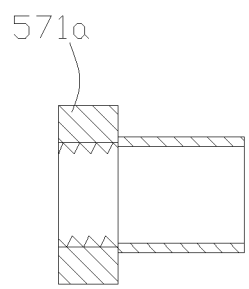
FIG. 33 is a sectional view of the connection member in FIG. 32.
Figure 34:
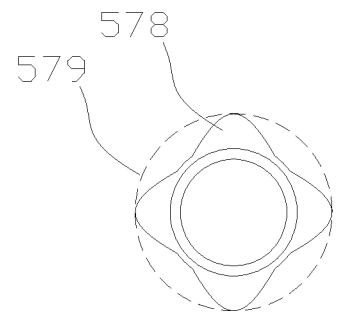
FIG. 34 is a top view of the proximal end side of the connection member in FIG. 32.

Referring to FIGS. 32 and 33, the connection member 57a is substantially the same as the connection member 57, but a difference lies in that the boss 571a of the connection member 57a has multiple small protrusions 578 distributed in an equal spaced-apart manner along its circumferential direction and connected with one another. Referring to FIG. 34, the multiple small protrusions 578 jointly form a virtual circumference 579 (namely a circumscribed circle of the multiple small protrusions 578 is 579). The diameter of the circumference 579 is the outer diameter of the boss 571a. Due to the existence of the small protrusions 578, a fastening position is provided for biopsy forceps, so that the biopsy forceps can clamp a connection apparatus more effectively to withdraw the elastic implant 500a. The connection between the connection member 57a and the connection part 52a may be implemented through techniques such as covering of a macromolecular thermal shrinkage tube or thin film, gluing, laser welding, soldering and the like.

It can be understood that, in other embodiments of the present disclosure, as the material of the second flexible section is the same as that of the elastic deformation part, the second flexible section can also be omitted, and the first flexible section is directly connected with the elastic deformation part, so no more details will be described here.

The embodiments of the present disclosure are described above in combination of the accompanying drawings, but the present disclosure is not limited to the above-mentioned specific implementation modes. The above-mentioned specific implementation modes are merely schematic, but not restrictive. Those of ordinary skill in the art can make many forms under the enlightenment of the present disclosure without departing from the purpose of the present disclosure and the scope protected by claims, and these forms shall all fall within the protection of the present disclosure.

The invention claimed is:

1. A lung volume reduction elastic implant, comprising an elastic deformation part and a flexible guide part connected with a distal end of the elastic deformation part, wherein the flexible guide part is provided with a first flexible section; the first flexible section comprises an insert section and a distal section; the insert section is connected with the distal end of the elastic deformation part; a distal end of the distal section of the first flexible section is a distal end of the lung volume reduction elastic implant; and wherein the flexible guide part further comprises a hollow second flexible section connected between the elastic deformation part and the first flexible section, the second flexible section having a lumen; and the insert section of the first flexible section is inserted into the lumen of the second flexible section;

wherein a radiograph component is arranged in the first flexible section, and a proximal end of the radiograph component is inserted into the lumen of the second flexible section along with the insert section of the first flexible section.

2. The lung volume reduction elastic implant according to claim 1, wherein the insert section has a radial height, and the radial height of the insert section of the first flexible section is less than that of the distal section, and a joint of the insert section and the distal section has a stepped shape.

3. The lung volume reduction elastic implant according to claim 1, wherein the radiograph component comprises a radiograph wire arranged in the first flexible section.

4. The lung volume reduction elastic implant according to claim 3, wherein the radiograph component further comprises a radiograph ring connected to a distal end of the radiograph wire.

5. The lung volume reduction elastic implant according to claim 1, wherein the second flexible section is more flexible from a distal end to a proximal end.

6. The lung volume reduction elastic implant according to claim 5, wherein the lung volume reduction elastic implant has a boss connected with a proximal end of the elastic deformation part, and part of a distal-end face of the boss is sunken towards a proximal end of the boss to form an annular groove surrounding the longitudinal center line of the boss.

7. The lung volume reduction elastic implant according to claim 5, wherein the lung volume reduction elastic implant has an opening in a proximal end and further includes a boss connected with a proximal end of the elastic deformation part, and part of a side surface of the boss is sunken into the inner of the boss to form an annular groove surrounding the longitudinal center line of the boss.

8. The lung volume reduction elastic implant according to claim 5, wherein the lung volume reduction elastic implant has an opening in a proximal end and further includes a boss connected with a proximal end of the elastic deformation part, and the boss comprises multiple small protrusions distributed in a spaced-apart manner along the circumferential direction of the boss.

9. The lung volume reduction elastic implant according to claim 1, wherein the lung volume reduction elastic implant has an opening in a proximal end and further includes a boss connected with a proximal end of the elastic deformation part; wherein a superelastic elastic deformation part is provided with a plurality of cutting slots in a spaced-apart manner along the longitudinal direction of the elastic deformation part; and the flexible guide part is more flexible than the elastic deformation part; and an outer diameter of the boss is greater than that of a part of the elastic implant close to the boss in a delivery state.

10. The lung volume reduction elastic implant according to claim 9, wherein the elastic implant further comprises a connection part located between the elastic deformation part and the boss; and the connection part is more flexible than the elastic deformation part.

11. The lung volume reduction elastic implant according to claim 10, wherein the connection part is provided with a plurality of cutting slots in a spaced-apart manner along the longitudinal direction of the connection part.

12. The lung volume reduction elastic implant according to claim 11, wherein the connection part comprises multiple hollow sub components connected end to end; a proximal end of each hollow sub component comprises multiple proximal end protrusions distributed along the circumferential direction of the hollow sub component; the circumferential length of each proximal end protrusion from a proximal end to a distal end is gradually decreased, and a proximal end groove is formed between two adjacent proximal end protrusions; a distal end of each hollow sub component comprises multiple distal end protrusions distributed along the circumferential direction of the hollow sub component; and the circumferential length of each distal end protrusion from a proximal end to a distal end is gradually increased, and a distal end groove is formed between two adjacent distal end protrusions.

13. A lung volume reduction instrument, comprising the implant according of claim 1 and a delivery apparatus matched with the implant, wherein the delivery apparatus comprises a core wire and a delivery mechanism; a proximal end of the implant is detachably connected to a distal end of the delivery mechanism; and the core wire may be movably arranged in, and extends through, a lumen of the implant and a lumen of the delivery mechanism.

14. The lung volume reduction instrument according to claim 13, wherein a core wire guide head coaxial with the core wire is arranged at a distal end of the core wire, and an outer diameter of the core wire guide head is consistent with that of the core wire.

15. The lung volume reduction instrument according to claim 14, wherein the core wire guide head comprises a guide column and a spring arranged surrounding the guide column; the guide column and the core wire are formed in one piece, or the guide column is fixedly connected to the distal end of the core wire; and the spring is provided with a radiopaque marker.

16. The lung volume reduction instrument according to claim 15, wherein the proximal end of the implant is detachably connected with the distal end of the delivery mechanism.

17. A lung volume reduction elastic implant, comprising an elastic deformation part and a flexible guide part connected with a distal end of the elastic deformation part, wherein the flexible guide part is provided with a first flexible section; the first flexible section comprises an insert section and a distal section; the insert section is connected with the distal end of the elastic deformation part; a distal end of the distal section of the first flexible section is a distal end of the lung volume reduction elastic implant; and a radiograph component is arranged in the first flexible section;

wherein the flexible guide part further comprises a hollow second flexible section connected between the elastic deformation part and the first flexible section; and the insert section of the first flexible section is inserted into a lumen of the second flexible section, and a proximal end of the radiograph component is inserted into the second flexible section along with the insert section of the first flexible section;

wherein the insert section has a radial height, and the radial height of the insert section of the first flexible section is less than that of the distal section, and a joint of the insert section and the distal section has a stepped shape; and wherein the proximal end of the radiograph component is closer to a distal end of the distal section than a proximal end of the insert section, and a perpendicular distance between the proximal end of the radiograph component and a proximal end of the first flexible section is 0.5 mm to 20 mm.

18. A lung volume reduction elastic implant, comprising an elastic deformation part and a flexible guide part connected with a distal end of the elastic deformation part, wherein the flexible guide part is provided with a first flexible section; the first flexible section comprises an insert section and a distal section; the insert section is connected with the distal end of the elastic deformation part; a distal end of the distal section of the first flexible section is a distal end of the lung volume reduction elastic implant; and a radiograph component is arranged in the first flexible section;

wherein the flexible guide part further comprises a hollow second flexible section connected between the elastic deformation part and the first flexible section; and the insert section of the first flexible section is inserted into a lumen of the second flexible section, and a proximal end of the radiograph component is inserted into the second flexible section along with the insert section of the first flexible section;

wherein the second flexible section is more flexible from a distal end to a proximal end; and wherein the second flexible section comprises a tubular body cut from a nickel-titanium tube and having continuous spiral cutting slots.

19. The lung volume reduction elastic implant according to claim 18, wherein a distance between two adjacent cutting slots of the second flexible section along the axial direction of the second flexible section is gradually increased from the distal end to the proximal end of the second flexible section.

\* \* \* \* \*